United States Patent
Kurkela et al.

(10) Patent No.: US 6,399,610 B1
(45) Date of Patent: Jun. 4, 2002

(54) TRANSMUCOSAL FORMULATIONS OF LEVOSIMENDAN

(75) Inventors: Kauko Kurkela, Espoo; Martti Marvola, Helsinki, both of (FI); Ilkka Larma, Springfield, NJ (US); Raimo Virtanen, Rusko; Marianne Karlsson, Helsinki, both of (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/581,610

(22) PCT Filed: Dec. 11, 1998

(86) PCT No.: PCT/FI98/00977

§ 371 (c)(1),
(2), (4) Date: Aug. 31, 2000

(87) PCT Pub. No.: WO99/32081

PCT Pub. Date: Jul. 1, 1999

(30) Foreign Application Priority Data

Dec. 19, 1997 (FI) .................................................. 974578

(51) Int. Cl.[7] ........................ A61K 31/50; A61K 9/14; A61F 13/02
(52) U.S. Cl. ...................... 514/249; 424/434; 424/435; 424/449; 424/451; 424/464
(58) Field of Search .......................... 514/247; 424/449, 424/434, 451, 464, 435

(56) References Cited

U.S. PATENT DOCUMENTS

| | | | | |
|---|---|---|---|---|
| 5,512,572 A | * | 4/1996 | Haikala et al. | 514/247 |
| 6,183,771 B1 | * | 2/2001 | Urtti et al. | 424/449 |

FOREIGN PATENT DOCUMENTS

| | | | |
|---|---|---|---|
| WO | WO 92/12135 | | 7/1992 |
| WO | WO 93/21921 | | 11/1993 |
| WO | WO-9630013 | * | 3/1995 |
| WO | WO 98/01111 | | 1/1998 |

* cited by examiner

*Primary Examiner*—Diana Dudash
*Assistant Examiner*—Mina Haghighatian
(74) *Attorney, Agent, or Firm*—Finnegan, Henderson, Farabow, Garrett & Dunner, L.L.P.

(57) ABSTRACT

A method of administering transmucosally, particularly to oral or nasal mucosa, levosimendan or a pharmaceutically acceptable salt thereof to a patient. The method comprises contacting an intact mucous membrane with a source of levosimendan, and maintaining said source with said mucous membrane for a sufficient time period to deliver levosimendan to the patient. Transmucosal preparations of levosimendan are also described. Levosimendan is useful in the treatment of heart failure.

9 Claims, 1 Drawing Sheet

TRANSMUCOSAL FORMULATIONS OF LEVOSIMENDAN

This application is a national stage filing of PCT International Application No. PCT/FI98/00977, filed Dec. 11, 1998, the content of which is incorporated herein by reference.

BACKGROUND OF THE INVENTION

The present invention relates to transmucosal delivery of levosimendan or a pharmaceutically acceptable salt thereof, particularly delivery via oral and nasal mucosa. The invention also relates to transmucosal, particularly intraoral and intranasal, e.g. buccal, sublingual or sinuidal, preparations comprising levosimendan or a pharmaceutically acceptable salt thereof as the active ingredient.

Levosimendan, which is the (-)-enantiomer of [[4-(1,4,5, 6-tetrahydro-4-methyl-6-oxo-3-pyridazinyl)phenyl] hydrazono]propanedinitrile (I), and the method for its preparation is described e.g. in EP 565546 B1. Levosimendan is potent in the treatment of heart failure and has significant calcium dependent binding to troponin. The use of levosimendan in the treatment of myocardial ischemia is described in WO 93/21921. Pharmacokinetics of levosimendan in man after i.v. and oral dosing is described in Sandell, E.-P. et al., J. Cardiovasc. Pharmacol., 26(Suppl. 1), S57-S62, 1995.

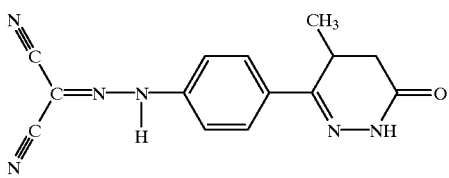

Clinical studies have confirmed the beneficial effects of levosimendan in heart failure patients.

SUMMARY OF THE INVENTION

It has now been found that therapeutically effective and steady serum levels of levosimendan are rapidly achieved by administering levosimendan transmucosally, preferably to oral or nasal mucosa. Furthermore, it has been found that by administering levosimendan transmucosally the occurence of undesired side effects such as headache and palpitation connected to the oral administration of levosimendan can be reduced or totally avoided. It is now believed that active metabolites formed in the gastrointestinal tract by intestinal bacteria contribute to the observed undesired effects. The formation of metabolites in the gastrointestinal tract can be reduced or totally avoided by transmucosal administration.

Accordingly, the object of the invention is to provide a method for administering transmucosally, i.e. to and across a mucosal surface, levosimendan or a pharmaceutically acceptable salt thereof. The mucosal surface is preferably oral or nasal mucosa such as the buccal mucosa, the sublingual mucosa, the sinuidal mucosa, the gum, or the inner lip.

The present invention also provides transmucosal, particularly intraoral and intranasal, e.g. buccal, sublingual or sinuidal, preparations comprising levosimendan or a pharmaceutically acceptable salt thereof as a therapeutically active ingredient.

The present invention also provides the use of levosimendan or a pharmaceutically acceptable salt there6f in the manufacture of a medicament for transmucosal administration, particularly to oral and nasal mucosa, of levosimendan or a pharmaceutically acceptable salt thereof.

Furthermore the present invention provides a method for treating heart failure comprising administering transmucosally, particularly to oral and nasal mucosa, a therapeutically effective amount of levosimendan or a pharmaceutically acceptable salt thereof to a subject in need of such treatment.

Furthermore the present invention provides a method of administering transmucosally, particularly to oral and nasal mucosa, levosimendan or a pharmaceutically acceptable salt thereof to a patient, wherein the method comprises contacting an intact mucous membrane with a source of levosimendan or a pharmaceutically acceptable salt thereof, and maintaining said source in contact with said mucous membrane for a sufficient time period to deliver said levosimendan or a pharmaceutically acceptable salt thereof to the patient.

DETAILED DESCRIPTION OF THE INVENTION

Figure 1:
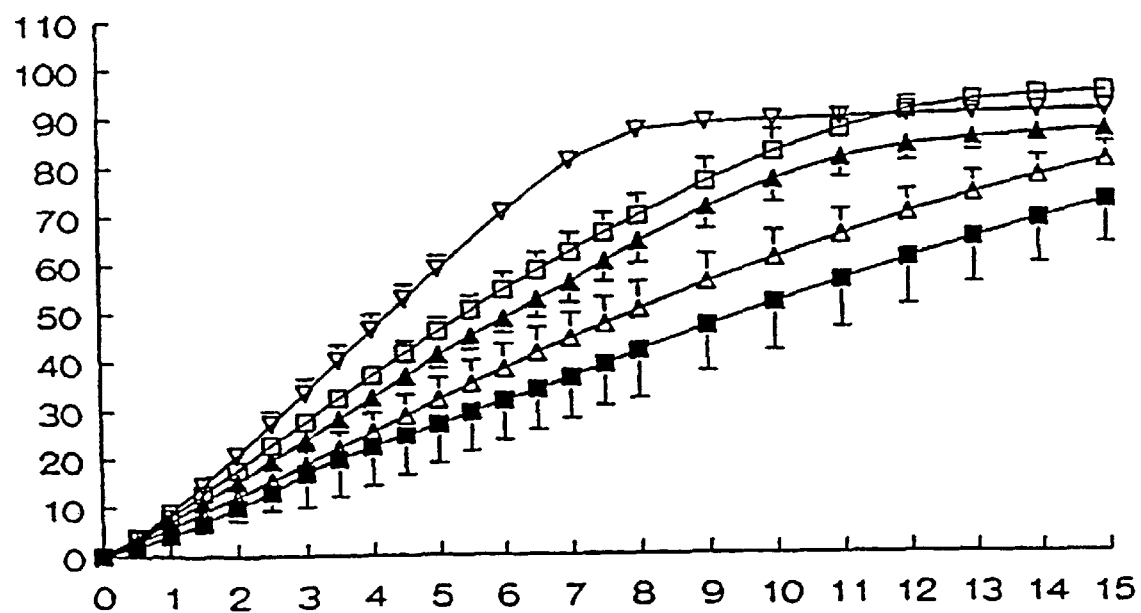
FIG. 1 illustrates the in vitro release of levosimendan from different mucoadhesive buccal preparations.

The transmucosal administration of levosimendan or a pharmaceutically acceptable salt thereof can be accomplished generally by contacting an intact mucous membrane with a source of levosimendan or a pharmaceutically acceptable salt thereof, and maintaining said source in contact with said mucous membrane for a sufficient time period to induce the desired therapeutic effect. Preferably the drug is administered to oral or nasal mucosa such as the buccal mucosa, the sublingual mucosa, the sinuidal mucosa, the gum, or the inner lip.

The precise amount of the drug administered according to the invention is dependent on numerous factors, such as age and body weight of the patient, the condition of the patient and the desired duration of use. The daily dose of levosimendan to human patients is within the range of about 0.1 to 500 mg, preferably 0.5 to 10 mg. The blood concentration of levosimendan in human patients can be about 1–300 ng/ml, preferably 10–150 ng/ml, especially 20–60 ng/ml. The time period for administering levosimendan from a sustained release preparation such as an transmucosal patch is from about 4 to 24 hours, typically about 12 hours.

The source of the drug can be any transmucosal preparation suitable for administering levosimendan or a pharmaceutically acceptable salt thereof. Particularly, the source of the drug is any preparation usable in oral, nasal, sinuidal or vaginal cavities that can be formulated using conventional techniques well known in the art. Preferred preparations are those usable in oral or nasal cavities. For example, the preparation can be a buccal tablet, a sublingual tablet, a spray, and the like preparation that dissolve or disintegrate, delivering drug into the mouth of the patient. A spray or drops can be used to deliver the drug to nasal or sinuidal cavities. Said preparation may or may not deliver the drug in a sustained fashion. The manufacture examples for such preparations are disclosed for example in U.S. Pat. No. 4,764,378.

Suitably the source of the drug is a mucoadhesive preparation. A. mucoahdesive preparation is a preparation which upon contact with intact mucous membrane adheres to said mucous membrane for a sufficient time period to induce the desired therapeutic effect. The preparation can be a semi-solid composition as described e.g. in WO 96/09829. It can be a tablet, a powder, a gel or film comprising a mucoadhesive matrix as described e.g. in WO 96/30013. The preparation can also be a syrup that adheres to the mucous membrane.

Suitable mucoadhesives include those well known in the art such as polyacrylic acids, preferably having the molecular weight between from about 450,000 to about 4,000,000, e.g. Carbopol™ 934P; sodium carboxymethylcellulose (NaCMC), hydroxypropylmethylcellulose (HPMC), e.g. Methocel™ K100, and hydroxypropylcellulose.

The preparation can also be in the form of a bandage, patch, device and the like preparation that contains the drug and adheres to a mucosal surface. Suitable transmucosal patches are described for example in WO 93/23011. A suitable patch may comprise a backing. The backing can be any flexible film that prevents bulk fluid flow and provides a barrier for to loss of the drug from the patch. The backing can be any of the conventional materials such as polyethylene, ethyl-vinyl acetate copolymer, polyurethane and the like. In a patch involving a matrix which is not itself a mucoadhesive, the drug-containing matrix can be coupled with a mucoadhesive component (such as a mucoadhesive described above) in order that the patch may be retained on the mucosal surface. Suitable configurations include a patch or device wherein the matrix has a smaller periphery than the backing layer such that a portion of the backing layer extends outward from the periphery of the matrix. A mucoadhesive layer covers the outward extending portion of the backing layer such that the underside of the backing layer carries a layer of mucoadhesive around its periphery. The backing and the peripheral ring of mucoadhesive taken together form a reservoir which contains a drug-containing matrix (e.g. a tablet, gel, or powder). It may be desirable to incorporate a barrier element between the matrix and the mucoadhesive in order to isolate the mucoadhesive from the matrix. The barrier element is preferably substantially impermeable to water and to the mucosal fluids that will be present at intended site of adhesion. A patch or device having such barrier element can be hydrated only through a surface that is in contact with the mucosa, and it is not hydrated via the reservoir. Such patches can be prepared by general methods well known to those skilled in the art.

Preparations usable according to the invention can contain pharmaceutical ingredients, such as fillers, lubricants, disintegrants, solubilizing vehicles, flavours, dyes and the like. It may be desirable in some instances to incorporate a mucous membrane penetration enhancer into the preparation. Suitable penetration enhancers include anionic surfactants (e.g. sodium lauryl sulphate, sodium dodecyl sulphate), cationic surfactants (e.g. palmitoyl DL camitine chloride, cetylpyridinium chloride), nonionic surfactants (e.g. polysorbate 80, polyoxyethylene 9-lauryl ether, glyceryl monolaurate, polyoxyalkylenes, polyoxyethylene 20 cetyl ether), lipids (e.g. oleic acid), bile salts (e.g. sodium glycocholate, sodium taurocholate),and related compounds.

The invention will be further clarified by the following examples, which are intended to be purely exemplary of the invention.

EXAMPLES

Example 1
Bioavailability of Levosimendan Following Buccal and Intravenous Administration in Dogs.

Bioavailability of levosimendan was studied in dogs following buccal and intravenous administration of 0.02 mg/kg of the compound. As experimental animals, three beagle dogs were used. At the time of dosing all animals weighed approximately 10 kg. The dogs were given levosimendan as an intravenous injection or buccal spray at one week intervals. Appropriate concentration (2 mg/ml in 96% ethanol) of the compound was prepared in 10 ml amber glass containers sealed with spray nozzles (50 µl dose, Pfeiffer). The 0.02 mg/kg buccal dose was thus obtained by spraying 2 consecutive 50 µl doses to the buccal cavity of the animals (the dosing volume being thus 0.1 ml/10 kg). The iv dose (0.1 ml/10 kg) was taken from the same bottles.

5 ml of blood was collected from the cephalic vein at the following times after administration: 0, 10, 20, 40, min, 1, 1.5 and 2 hours. Plasma was separated and stored frozen in −20 ° C. until analyzed.

Determination of Levosimendan in Dog Plasma

Levosimendan in dog plasma was determined by a non-enantioselective method, in which an automated sample preparation technique combined with high performance liquid chromatography was used. The plasma clean-up was performed by on-line dialysis and the, dialysate was retained on a trace enrichment column. The analyte was then-separated on an analytical column and detected with a UV-detector. The limit of quantitation was 5 ng/ml and the quantitation range 5–500 ng/ml.

The apparatus comprised a Gilson ASTED (Automated Sequential Trace Enrichment System) system (Gilson Medical Electronics, Villiers-le-Bel, France). The dialysis cell was fitted with a Cuprophan cellulose membrane with a molecular cut-off of 15 kDa and the trace enrichment column was a Hypersil ODS (5.8×4.6 mm i.d., 10 µm). The chromatographic system consisted of an LKB Model 2150 pump (Bromma, Sweden) and a Lichrosorb RP-18 (250×4 mm i.d., 10 µm) column (Merck, Darmstadt, Germany). The detector was a Spectra 100 UV-VIS (Spectra-Physics, San Jose, Calif., USA). The wavelength was 380 nm. The mobile phase consisted of a 32 mM monosodium dihydrogen phosphate buffer, methanol, and tetrahydrofuran (45:65:1, v/v/v, pH 3.5). The mobile phase flow rate was 1.0 ml/min.

The results are shown in table 1.

TABLE 1.

Levosimendan concentrations in dog plasma after buccal and intravenous (iv) administration.

| | Levosimendan concentration (ng/ml) | | |
|---|---|---|---|
| Time (min) | Dog 1 | Dog 2 | Dog 3 |
| Buccal: | | | |
| 0 | < | < | < |
| 10 | 10 | 17 | 7.6 |
| 20 | 24 | 24 | 9.4 |
| 40 | 32 | 25 | 25 |
| 60 | 26 | 22 | 24 |
| 90 | 18 | 17 | 22 |
| 120 | 13 | 12 | 16 |
| iv: | | | |
| 0 | < | < | < |
| 10 | 128 | 103 | 100 |
| 20 | 105 | 71 | 82 |
| 40 | 74 | 46 | 58 |
| 60 | 58 | 36 | 46 |
| 90 | 39 | 24 | 33 |
| 120 | 28 | 15 | 25 |

< means below quantitation range

Table 1 shows that levosimendan is rapidly absorbed into blood from the buccal spray and steady serum levels of levosimendan are obtained.

Example 2
Preparation of Mucoadhesive Buccal Tablets and in Vitro Release Experiment Five different mucoadhesive buccal tablet formulations of levosimendan were prepared according to Table 2.

TABLE 2.

Five different mucoadhesive buccal tablet formulations of levosimendan

| Constituent | Amount (mg) | | | | |
|---|---|---|---|---|---|
| | I | II | III | IV | V |
| Levosimendan | 2 | 2 | 2 | 2 | 2 |
| HPMC K100 78 | 42.9 | 70.2 | 62.4 | 70.2 | — |
| Lactose | — | 31.2 | — | — | — |
| Carbopol ™ 934P | — | 3.9 | — | — | — |
| NaCMC ulv | — | — | 7.8 | 15.6 | — |
| NaCMC lv | — | — | — | — | 7.8 | ulv = ultra low viscosity
lv = low viscosity

Buccal tablets described above were prepared by mixing powders needed for a batch of desired size in Turbula mixer and pressing in a tablet press using 7 mm punchs and 5–8 kN compression force. The thickness of the tablets was about 1.8 mm.

The release of levosimendan from the preparations was studied using the paddle method according to USP XXII. The dissolution medium was phosphate buffer pH 5.8. The rotation speed of the paddles 50 rpm.

FIG.1 shows the release (%) of levosimendan vs. time (h) from the buccal tablets of Table 2. All preparations acted as long-acting preparations. Preparations I, II, III and V released levosimendan according to zero order kinetics up to 10 hours. The addition of NaCMC increased the release of levosimendan from buccal tablets. The figure shows that the position of the release curve may be systematically adjusted with the aid of amount and type of the mucoadhesive polymer. The legends in FIG.1 mean Δ formulation I
■ formulation II
□ formulation III
▽ formulation IV
▲ formulation V

What is claimed is:

1. A transmucosal preparation comprising levosimendan or a pharmaceutically acceptable salt thereof as a therapeutically active ingredient, together with one or more pharmaceutically acceptable excipients.

2. A preparation according to claim 1 which upon contact with intact mucous membrane adheres to said mucous membrane for a sufficient time period to induce the desired therapeutic effect.

3. A preparation according to claim 1, which is in the form of a mucoadhesive preparation.

4. A preparation according to claim 1, which comprises a mucoadhesive matrix.

5. A preparation according to claim 1, which is in the form of a patch.

6. A method for treating heart failure comprising administering transmucosally a therapeutically effective amount of levosimendan or a pharmaceutically acceptable salt thereof to a subject in need of such treatment.

7. A method of administering levosimendan or a pharmaceutically acceptable salt thereof transmucosally to a patient, which comprises contacting an intact mucous membrane of the patient with a source of levosimendan or a pharmaceutically acceptable salt thereof, and maintaining said source in contact with said mucous membrane for a sufficient time period to deliver said levosimendan or a pharmaceutically acceptable salt thereof to the patient.

8. A method as claimed in claim 6, wherein the levosimendan or pharmaceutically acceptable salt thereof is administered to the oral or nasal mucosa.

9. A method as claimed in claim 7, wherein the intact mucous membrane is an oral or nasal mucous membrane.

* * * * *